(12) United States Patent
Hisanaka et al.

(10) Patent No.: US 6,395,122 B1
(45) Date of Patent: May 28, 2002

(54) APERTURED WEB FOR DISPOSABLE BODY EXUDATES ABSORBENT GARMENTS AND METHOD FOR MAKING SAME

(75) Inventors: Takayuki Hisanaka; Hisashi Takai; Koichi Yamaki, all of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/418,421

(22) Filed: Oct. 15, 1999

Related U.S. Application Data

(62) Division of application No. 09/199,956, filed on Nov. 25, 1998, now Pat. No. 6,117,524.

(30) Foreign Application Priority Data

Nov. 26, 1997 (JP) .............................................. 9-324591
Sep. 9, 1998 (JP) ........................................... 10-254980

(51) Int. Cl.[7] .............................................. B32B 31/00
(52) U.S. Cl. ........................ 156/268; 83/861; 83/865; 83/33; 83/39; 156/270; 156/271; 156/254
(58) Field of Search ............................... 156/268, 270, 156/257, 523, 271, 254; 83/861, 865, 39, 53

(56) References Cited

U.S. PATENT DOCUMENTS 4,276,336 A 6/1981 Sabee ......................... 428/132
4,591,523 A * 5/1986 Thompson ................... 428/131
5,142,750 A 9/1992 Dyer et al. ................... 26/29 R
5,635,276 A 6/1997 Biagioli et al. .............. 428/132

FOREIGN PATENT DOCUMENTS

| DE | 37 23 404 | 1/1989 |
| EP | 0 545 423 | 6/1993 |
| GB | 2 312 625 | 11/1997 |
| JP | A 62-57551 | * 3/1987 |

OTHER PUBLICATIONS

Copy of European Search Report, EP 98 30 9685, dated Aug. 24, 2000.

* cited by examiner

*Primary Examiner*—Linda Gray
(74) *Attorney, Agent, or Firm*—Baker & Daniels

(57) ABSTRACT

A method for manufacturing an aperture web including bonding a first and second web together with the second web bonded to a lower surface of the first web and feeding the bonded web in a first direction, subjecting the first web to pillar-shaped water jets from at least one nozzle having a plurality of orifices arranged transversely to the first direction until the first web is locally torn and provided with a plurality of apertures in rows extending parallel to one another in the first direction, and then subjecting the second web to pillar-shaped water jets supplied from at least one nozzle having a plurality of orifices arranged transversely to the first direction until peripheral edges of the apertures are partially deformed upward from the lower surface of the first web.

10 Claims, 5 Drawing Sheets

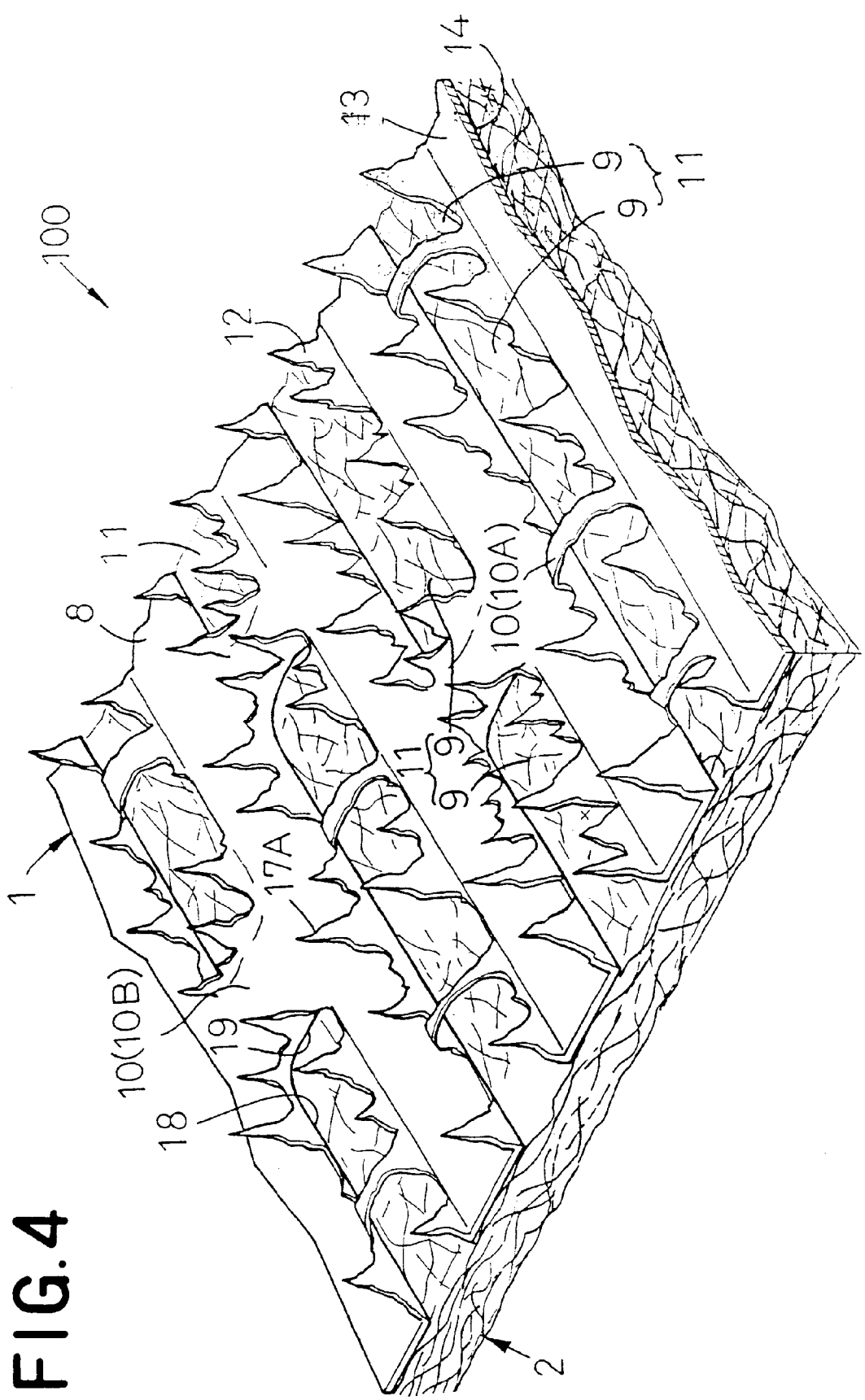

APERTURED WEB FOR DISPOSABLE BODY EXUDATES ABSORBENT GARMENTS AND METHOD FOR MAKING SAME

This is a Divisional of application Ser. No. 09/199,956, filed Nov. 25, 1998 now U.S. Pat. No. 6,117,524.

BACKGROUND OF THE INVENTION

This invention relates to apertured webs for body exudates absorbent garments such as skin-contactable sheets for disposable diapers and sanitary napkins.

FIG. 8 of the accompanying drawings is a perspective view of a microapertured polymeric web 110 described in Japanese Patent Application Disclosure Gazette (Kokai) No. Sho62-57551 in which the web 110 exhibiting a substantially uniform soft and silky tactile impression. The web 110 is intended to be used as a topsheet or a backsheet in a disposable diaper and made from a relatively thin plastic material as a starting web. Specifically, the starting web is placed on a support such as a mesh wire and transported into a processing zone in which the starting web is subjected to high pressure liquid jets.

The apertured polymeric web 110 is formed on its skin-contactable surface with a plurality of cylindrical projections 120 which have, in turn, microapertures 125 at their tops. Each of these microapertures 125 is formed along its peripheral edge with irregularly shaped petals. The web 110 is claimed to have a soft fabric-like touch and to present no surface gloss.

Whether the polymeric web used in disposable diapers or sanitary napkins present a soft touch or not when such web is in contact with the wearer's skin is often determined on the basis of a certain softness reference, for example, softness of a woven or nonwoven fabric made of natural fibers or synthetic fibers.

In the polymeric web, a peripheral edge of each microaperture formed at the top of each cylindrical projection is finely divided so as to form the irregularly shaped petals. Probably the irregularly shaped petals provide a soft fabric touch when the wearer's skin rubs the irregularly shaped petals. However, even when the polymeric web is formed with a plurality of the cylindrical projections, there is an apprehension that these projections may rather increase a rigidity of the web. Accordingly, it is difficult for the polymeric web to reconcile a high softness and a high drapeability as provided by a woven- or nonwoven fabric. A topsheet in a body exudates absorbent garment can comfortably adopt itself to the wearer's skin only when the softness and drapeability are well reconciled.

A drapeability of the polymeric web can be improved by thinning the polymeric web. For example, use of low density polyethylene having a thickness of 0.001~0.020 mm as the topsheet in disposable diapers or sanitary napkins will be effective to improve the drapeability. However, such excessively thin web will inevitably confront problems such that the web must be handled with excessive carefulness during the process for manufacturing diapers or napkins and the web can not be easily peeled off from the wearer's skin once the web has been electrostatically attracted on the wearer's skin.

SUMMARY OF THE INVENTION

In view of the above problems, the invention first aims to improve a drapeability of the conventional polymeric web having a soft fabric-like touch. The invention further aims to facilitate the relatively thin polymeric web having its drapeability improved to be handled during the process of manufacturing disposable garments. The invention additionally aims to provide a method for manufacturing the polymeric web having a softness as well as a high drapeability and having its handling facilitated.

According to first and second aspects of the invention, respectively, as will be described below:

The first aspect of the invention relates to an apertured web for a disposable garment, the apertured web comprising: an apertured polymeric web having upper and lower surfaces, the apertured polymeric web being 0.001~0.05 mm and including a plurality of substantially flat portions, each being 0.03~1 mm wide, extending in parallel one to another in one direction and a plurality of intermittent apertures extending in the one direction between each pair of the flat portions so as to form a plurality of aperture rows extending in parallel one to another in the one direction; the flat portions adjacent one to another with the aperture rows therebetween being interconnected by a plurality of bridge-like portions extending both of the flat portions adjacent one to another across the aperture rows; and the intermittent apertured being defined by edges of the flat portions extending in the one direction and edges of the bridge-like portions extending transversely of the flat portions, the flat portions being formed at least along the edges thereof extending in the one direction with a plurality of substantially saw-tooth-shaped rising portions rising upward from the upper surface of the flat portions so as to make the upper surface more rough than the lower surface of the flat portions.

The first aspect of the invention includes preferable embodiments as follows:

(1) Most of the intermittent apertures have a width of 0.07~1 mm and a length corresponding to 1.5 or more times of the width.

(2) A tension exerted on the web transversely of the aperture rows causes only the bridge-like portions to be stretched and thereby causes the web to be stretched transversely of the aperture rows.

(3) A fibrous layer having a basis weight of 2~30 $g/m^2$ is joined to the lower surface of the polymeric web to form a composite web.

(4) The fibrous layer comprises thermoplastic synthetic fibers or chemical fibers having a fineness of 1~15 d.

(5) The fibrous layer includes natural fibers.

(6) The fibrous layer comprises hydrophilic fibers.

(7) The polymeric web is formed with a plurality of liquid guiding passages each having a diameter of 0.1~5 mm and extending downward from the upper surface.

The second aspect of the invention relates to a method for continuously manufacturing an apertured web composed of an apertured polymeric web as first web having upper and lower surfaces, sheet-like fibrous assembly as a second web having upper and lower surfaces, the upper surface of the second web being joined to the lower surface of the first web, and a plurality of rising portions formed on the upper surface of the first web by a part of the first web so as to make the upper surface of the first web rough, the method comprising the steps of:

a. continuously feeding the first web in one direction;

b. continuously feeding the second web in the one direction so that the upper surface of the second web is placed upon the lower surface of the first web, followed by joining these first and second webs together under a pressure to form a first composite web;

c. continuously feeding the first composite web in one direction so that the upper surface of the first web as one component of the first composite web is subjected to pillar-shaped water jets supplied from nozzle means having a plurality of fine orifices arranged transversely of the one direction and, if desired, the upper surface of the first web is repeatedly subjected to the pillar-shaped water jets describing their corresponding loci substantially aligned one with another until the first web is at least locally torn along the loci, thereby the first web is formed with a plurality of aperture rows extending in parallel one to another in the one direction and second composite web is obtained; and d. continuously feeding the second composite web in one direction so that the lower surface of the second web as the other component of the second composite web is subjected to pillar-shaped water jets supplied from nozzle means having a plurality of fine orifices arranged transversely of the one direction, using pillar-shaped water jets preferably arranged so as to describe their loci substantially aligned with the loci described by the corresponding pillar-shaped water jets on the step c, more preferably two or more times, until the first web is partially deformed substantially in the sawtooth-shape upward from the lower surface of the first web along peripheral edges of the apertures in the respective aperture rows which have been formed as a result of local tearing of the first web under the effect of the pillar-shaped water jets.

The second aspect of the invention includes preferable manners of execution as follows:

(1) The step b comprises a step of pressing the first web in its thermally softened state against the second web.

(2) The step b comprises a step of feeding the first web together with a second web into a nip between a pair of heated rolls to heat-seal these two webs.

(3) The step b comprises a step of bonding the first and second webs together by means of adhesive agent.

(4) The first web includes any one of the thermoplastic synthetic fibers, chemical fibers and natural fibers.

(5) The method further including a step of making the second web hydrophilic.

BRIEF DESCRIPTION OF THE DRAWINGS

FIG. 4 is a perspective view showing an embodiment of composite web incorporated with the polymeric web as a component;

DESCRIPTION OF THE PREFERRED EMBODIMENTS

An apartured web according to the invention particularly intended to be used in disposable garments as well as a method for making such a web will be more fully described with reference to the accompanying drawings.

Figure 1:
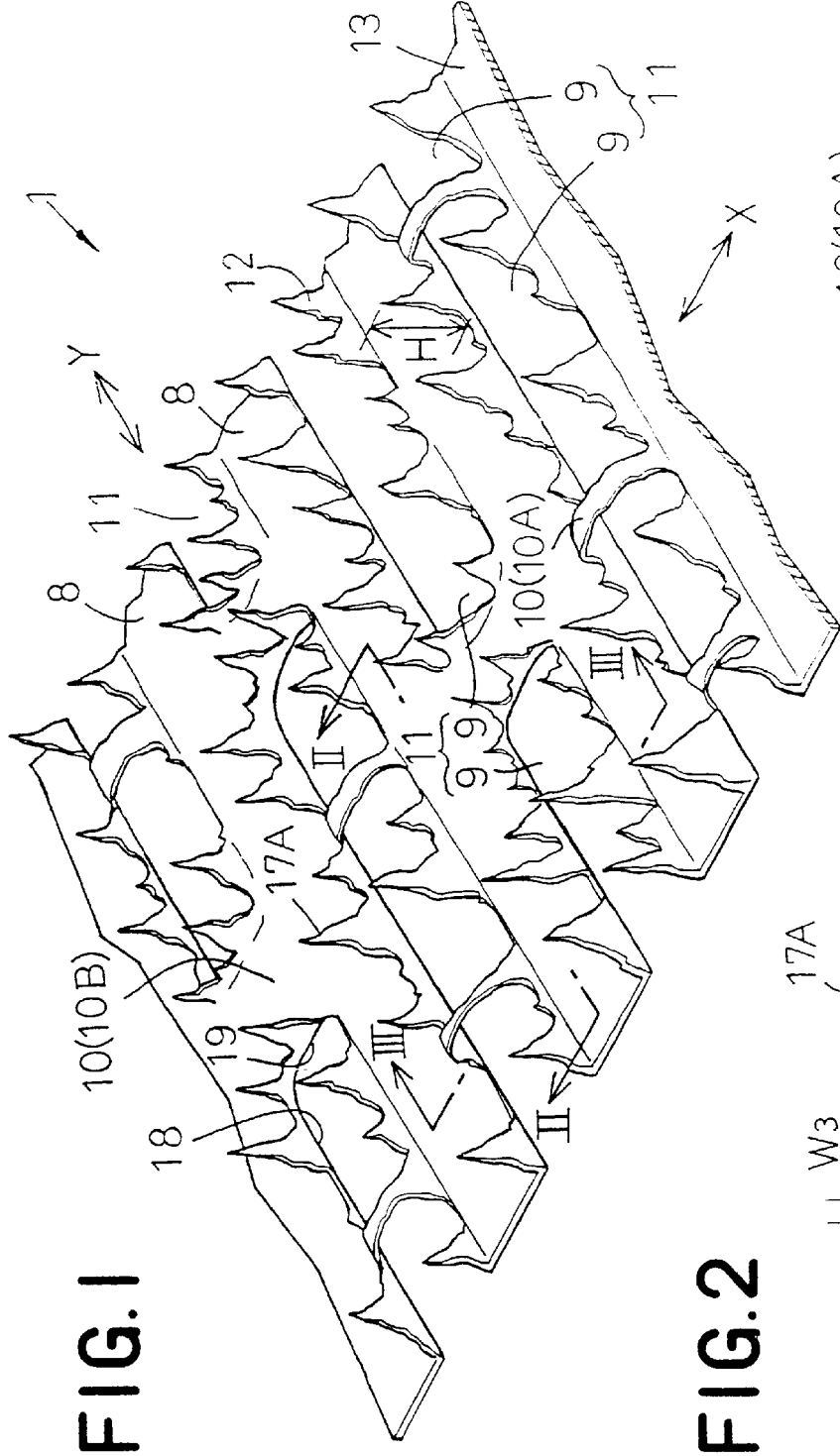
FIG. 1 is a perspective view of polymeric web according to the invention.

A polymeric web 1 shown by FIG. 1 in a perspective view is made of a thermoplastic synthetic resin film and has a flexibility. The web 1 comprises a plurality of substantially flat portions 8 extending in parallel one to another in a direction as indicated by a double-headed arrow Y, a plurality of aperture rows 11 extending also in the direction Y. Each of the apertures rows 11 includes aperture 9 defined between each pair of the adjacent flat portions 8, bridge-like portions 10 extending across the respective apertures 9 between each pair of the adjacent flat portions 8, and a plurality of raised portions 12 formed on edges of the apertures 9 so as to extend upward with respect to upper surfaces 13 of the flat portions 8. A thickness of the web 1 should be understood to be a thickness of the flat portions 8.

Figure 3:
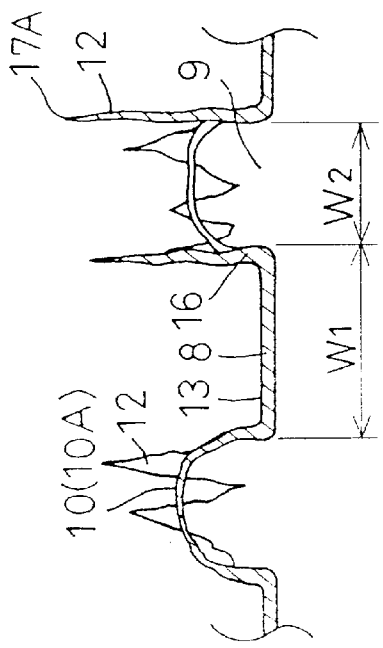
FIG. 3 is sectional view taken along a line III—III in FIG. 1.
Figure 2:
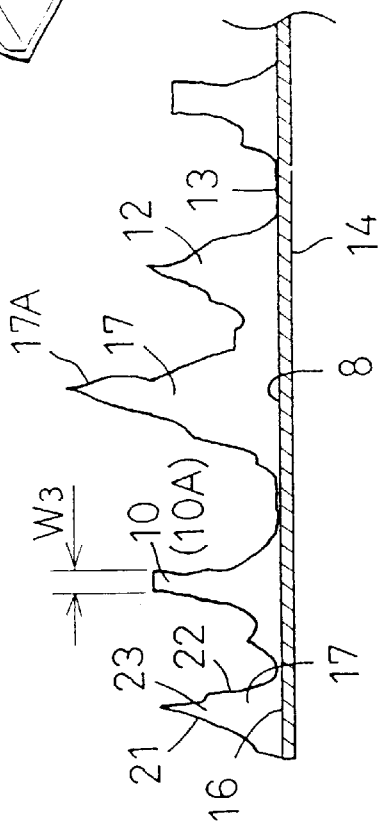
FIG. 2 is a sectional view taken along a line II—II in FIG. 1.

FIGS. 2 and 3 are sectional view taken along lines II—II and III—III, respectively, in FIG. 1. Each of the flat portions 8 has a thickness of 0.001~0.05 mm and a width $W_1$ of 0.03~1 mm as measured in a direction as indicated by a double-headed arrow X between a pair of the adjacent apertures 9, 9. A plurality of the apertures 9 are formed intermittently in the direction Y so as to define each of the aperture rows 11. Each of these apertures 9 preferably has a width $W_2$ of 0.07~1 mm corresponding to 1.5 or more times of its length. The bridge-like portions 10 extending across the respective apertures rows 11 are formed intermittently in the direction Y. There are provided two types of these bridge-like portions 10, i.e., those (10A) which extend upward or downward from the upper surfaces 13 of the flat portions 8 to the upper surfaces 13 of the respectively adjacent flat portions 8 so as to describe arcs and those (10B) which are flush with the flat portions 8. Preferably, each of the bridge-like portions 10A has a width $W_3$ of at least 0.01~2 mm as measured in the direction Y. Each of the rising portions 12 is formed by partially folding the flat portion 8 upward along the edge of the aperture 9 and has a proximal end 16 connected to the flat portion 8 and a free end 17 extending upward from the proximal end 16. Each of the apertures 9 is defined by edges 18 extending substantially in the direction Y and edges 19 extending substantially in the direction X. An upper edge 17A of the free end 17 forms irregularly shaped petals at least along the edge 18. The upper edge 17A lies at a height H of 0~1 mm as measured from the upper surface 13 of the flat portion 8.

Such irregularly shaped petals of the upper edge 17A occurs, for example, in a manner as seen in FIG. 2. Specifically, a substantially triangular zone 23 defined by an oblique side 21 ascending substantially rightward, an oblique side 22 ascending substantially leftward and the proximal end 16 extending between these two oblique sides 21, 22 repeatedly appears. A thickness of the rising portion 12 should be equal to or less than the thickness of the flat portion 8 so that, upon contacting the wearer's skin, the rising portion 12 may be flexibly deformed and give the upper surface of the web 1 soft and smooth velvet touch.

While it is difficult to visibly identify each of the rising portions 12, these rising portions 12 entirely make the upper surface of the web 1 fluffy and give the upper surface somewhat rough appearance. Over such upper surface of the web 1, light rays incident thereupon are diffusively reflected by the rising portions 12 and the upper surface is correspondingly less glossy than the lower surface of the web 1. In this manner, the rising portions 12 are effective to reduce surface gloss peculiar to the smooth polymeric web 1. Such effect of reducing the surface gloss will be further improved when the respective flat portions 8 are provided on their upper surface 13 with a plurality of fine irregularities formed by embossing.

The polymeric web 1 can be easily folded along the aperture rows 11 with a high drapeability. If most of the apertures 9 have their lengths 1.5 or more times of their widths, the drapeability will be further improved. Expression "most" should be understood to mean 70% or higher, preferably 80% or higher and more preferably 90% or higher of the total number of these apertures 9. When the web 1 includes the bridge-like portions 10 which describe the arcs bulging upward or downward from the upper surfaces 13 of the respective flat portions 8 (i.e., in the case of the bridge-like portions 10A), these arcs are flattened as the web 1 is subjected to a tension in the direction X orthogonal to the aperture rows 11 and therefore the web 1 is stretchable in the direction X. Depending on the material for the web 1, the stretchability of the bridge-like portions 10 is high particularly when each of the bridge-like portions 10 has a width of 0.001~0.1 mm. Stretchability of the web 1 also contributes to improvement of its drapeability.

It has been found that the web 1 can be used as the most suitable liquid-permeable topsheet in disposable diapers or sanitary napkins when its air-permeability is adjusted to 50~700 mm$^3$/cm$^2$·sec as measured according to JIS (Japanese Industries Standards)-L-1096 and its liquid-resistance is adjusted to 0~200 mm as measured according to JIS-L-1092.

FIG. 4 is a perspective view of a composite web 100, exemplarily showing a manner in which the web 1 is used. The web 1 itself is relatively thin and it may be difficult to handle it during the manufacturing process for disposable diapers or sanitary napkins. The web 1 is apt to be torn along the aperture rows 11 and such tendency also makes it difficult to handle the web 1. Furthermore, once the lower surface 14 of the web 1 has been tightly attracted onto the wearer's skin under the electrostatic effect, it will be inconveniently difficult to peel off the web 1 from the skin. To avoid such problems, a fibrous layer 2 is joined to the lower surface 14 of the web 1 as in the embodiment shown by FIG. 4 so that a thickness of the web 1 may be increased without loss of a desired touch peculiar to the rising portions 12 and at the same time a tear strength of the web 1 may be improved. Improvement of the tear strength facilitates the web 1 to be handled.

The fibrous layer 2 preferably has a basis weight of 2~30 g/m$^2$ and is made of thermoplastic synthetic fibers, chemical fibers such as rayon fibers, a mixture of these synthetic fibers and chemical fibers or a mixture of the synthetic fibers or chemical fibers and natural fibers such as cotton fibers or pulp fibers. The fibrous layer 2 preferably is a nonwoven fabric made of any one of the fibers or a mixture thereof and presents a flexibility. More preferably, the fibrous layer 2 is a nonwoven fabric made of thermoplastic synthetic fibers having a fineness of 0.1~15 d. It should be understood here that such a nonwoven fabric includes a nonwoven fabric made of melt blown fibers.

When the composite web 100 is used as a liquid-permeable topsheet in disposable diapers or sanitary napkins, it is preferable that the composite web 100 has an air-permeability of 50~700 mm$^3$/cm$^2$·sec as measured in the thickness direction of the fibrous layer 2 according to JIS-L-1096 and a liquid-resistance of 0~200 mm as measured according to JIS-L-1092. In addition, the fibrous layer 2 is preferably made of hydrophilic fibers. The web 1 and the fibrous layer 2 may be joined together by means of heat- or ultrasonic-sealing technique or suitable adhesive agent such as hot melt adhesive.

The polymeric web 1 as well as the composite web 100 as have been described above can be advantageously used as the liquid-permeable topsheet in the body exudates absorbent garment for the reason as follows: Body exudates discharged on the flat portions 8 flow through a valley defined between each pair of the rising portions 12 which are adjacent to each other in the direction Y into the adjacent aperture 9, on one hand, and directly flow into the apertures 9 at locations of the flat portions 8 having no rising portion 12 along their side edges (i.e., the locations at which the height of the rising portions 12 is substantially zero), on the other hand. In this way, the body exudates can be rapidly absorbed by the core. Accordingly, both the web 1 and the composite web 100 are free from any apprehensive inconvenience that any amount of body exudates stay on the upper surface of the web 1 after discharged whether the rising portions 12 are present or not around the apertures.

Figure 5:
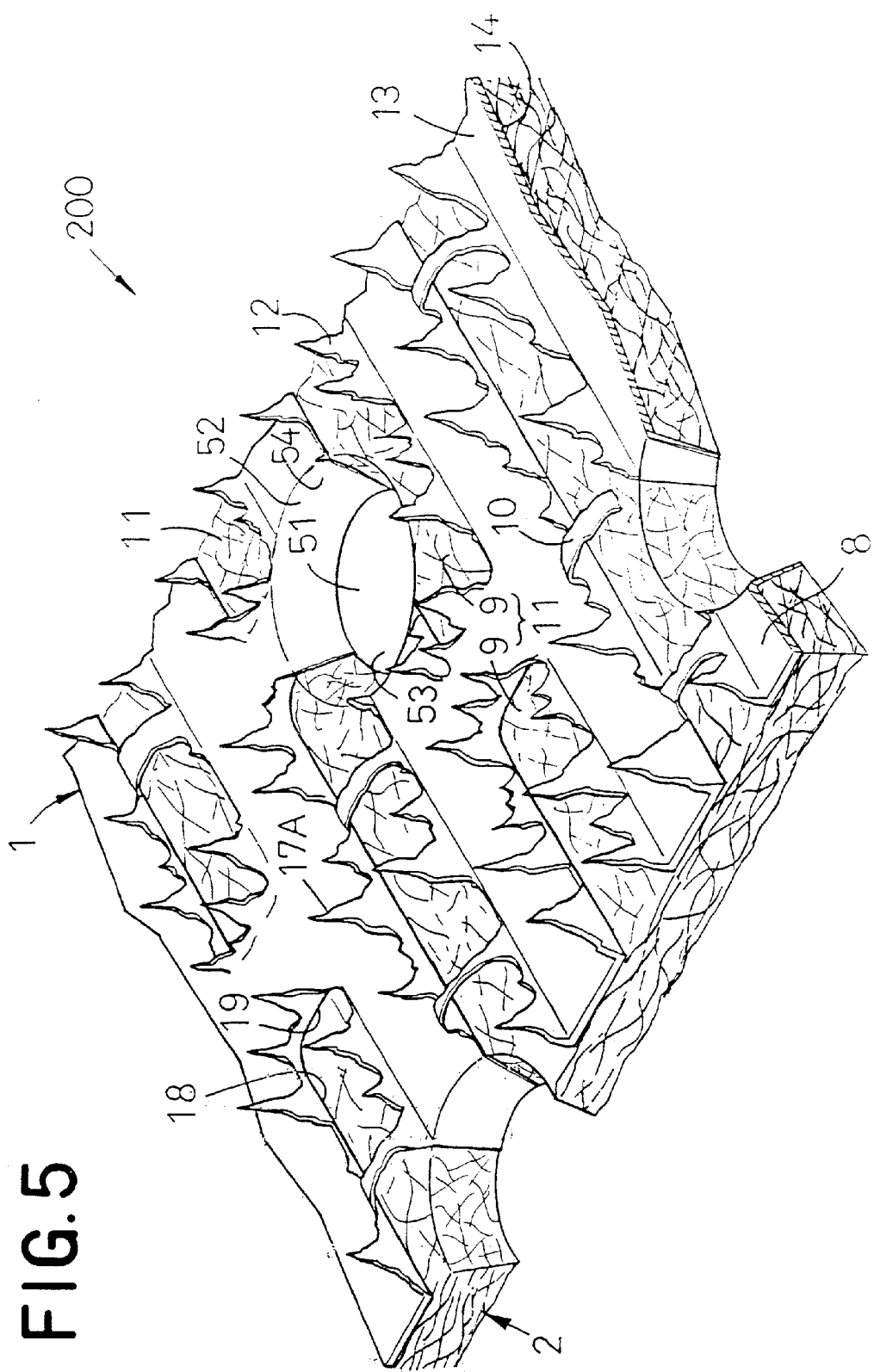
FIG. 5 is a perspective view showing another embodiment of the composite web incorporated with the polymeric web as a component.

FIG. 5 is a view similar to FIG. 4 showing an alternate manner in which the web 1 is actually used in the form of composite web 200. While this composite web 200 also comprises the web 1 and the fibrous layer 2 just as in the case of the composite web 100, the web 1 used as a component of this composite web 200 includes liquid guiding passages 51 in addition to the arrangement shown by FIG. 1. Each of the liquid guiding passages 51 has a tubular configuration extending from the upper surface to the lower surface of the web 1. More specifically, the liquid guiding passage 51 comprises an upper opening 52, a lower opening 53 and a tubular wall 54 extending between these two openings 52, 53. Each of these openings 52, 53 has a diameter of 0.1~5 mm, more preferably of 1.5~5 mm. An open area ratio of the upper openings 52 to the upper surface of the web 1 is 1~70%, more preferably 5~50%. The liquid guiding passage 51 has a length of 0.1~5 mm, more preferably 0.2~3 mm. While the fibrous layer 2 is shown to cover the lower surface 14 of the web 1 only its zone extending around the lower openings 53 of the respective liquid guiding passages 51, it is also possible to cover the lower surface 14 inclusive of all the lower openings 53.

Such composite web 200 is suitable particularly for use as the topsheet in disposable diapers or sanitary napkins. So far as the lower openings 53 are in contact with the liquid-absorbent core of diapers or napkins, body exudates discharged on diapers or napkins can be rapidly guided by the liquid guiding passages 51 to the core. To ensure such liquid guiding effect, it is preferable that each of the liquid guiding passages 51 is tapered from its upper opening 52 to its lower opening 53 and at least an inner surface of its tubular wall 54 is hydrophilic.

Figure 6:
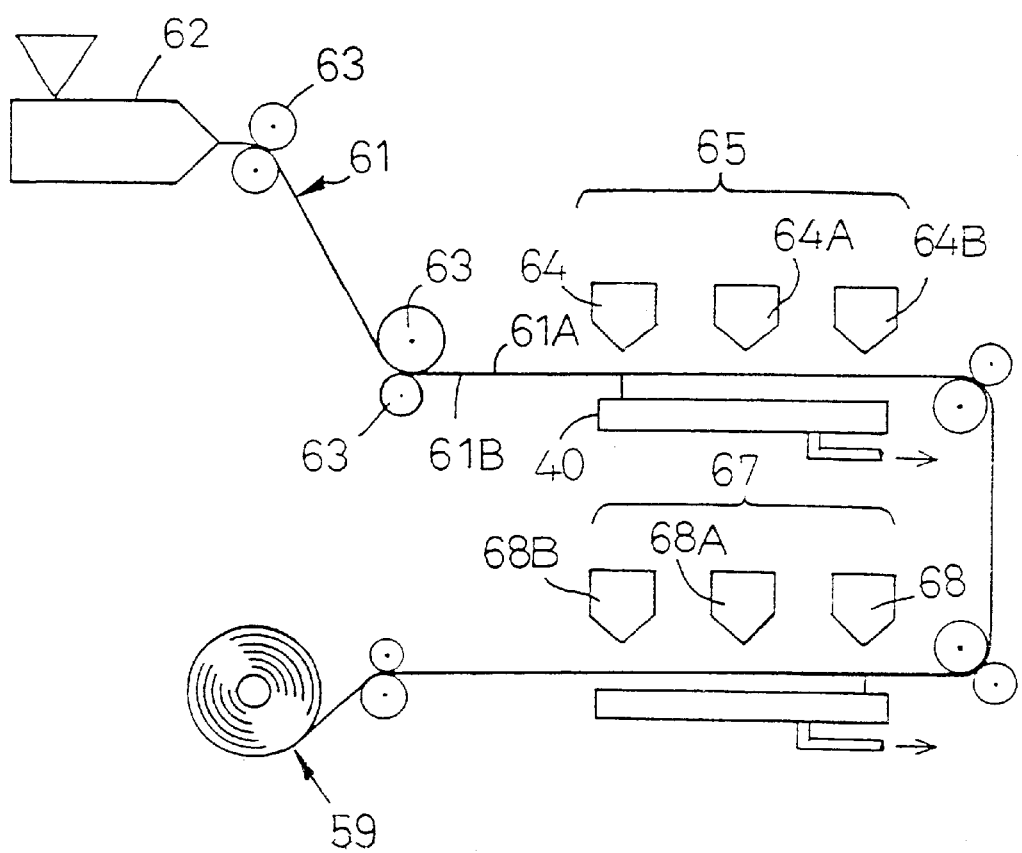
FIG. 6 is a diagram schematically illustrating a manufacturing process for a continuous polymeric web.

FIG. 6 is a diagram exemplarily illustrating a process according to which the web 1 is manufactured.

Starting from the left hand in FIG. 6, a web 61 of thermoplastic synthetic resin film is discharged from an extruder 62 and then fed by feed rolls 63 to a first processing zone 65. In the first processing zone 65, the web 61 has its upper surface 61A subjected to a plurality of pillar-shaped water jets supplied from a nozzle array 64 having a plurality of orifices arranged at a predetermined pitch transversely of the web 61. The web 61 is torn at its spots directly impinged by the pillar-shaped water jets or in the vicinity of these spots and consequently a plurality of intermittent apertures (not shown) are formed longitudinally of the web 61 as the latter travels so as to form a plurality of aperture rows (not shown) extending in parallel one to another transversely of the web 61. In this manner, a continuous web 59 is obtained. The web 59 corresponds to the web 1 shown by FIG. 1 and the intermittent apertures forming the aperture rows correspond to the apertures 9 and the aperture rows 11, respectively, shown by FIG. 1. The first processing zone 65 may include, in addition to the nozzle array 64, second and third nozzle arrays 64A, 64B adapted to supply pillar-shaped water jets, if necessary to form the aperture rows. These nozzle arrays 64,64A, 64B are preferably arranged so that corresponding orifices of these nozzle arrays are substantially aligned one with another transversely of the web 61 and therefore the corresponding orifices describe loci which are substantially placed one upon another. Below the first processing zone 65, there is provided a suction mechanism 40 adapted to collect the amount of water jetted from the respective nozzle arrays under an effect of suction. Lower surfaces 61B of the web 61 in FIG. 6 corresponds to the upper surface of the web 1 in FIG. 1.

The web 61 which has been formed with the apertures in the first processing zone 65 may be then subjected to the pillar-shaped water jets supplied from, instead of the second and third nozzle arrays 64A, 64B in the same zone 65, a fourth nozzle array 68 alone or fourth, fifth and sixth nozzle arrays 68, 68A, 68B in a second processing zone 67 which underlies the lower surface 61B of the web 61 so far as the water jets supplied from these nozzle arrays 68, 68A, 68B describe loci substantially placed upon the loci described by the water jets supplied from the first nozzle array 64. In this case, peripheral edges of the respective apertures are deformed in a direction of the pillar-shaped water jets to which the web 61 is subjected in the second processing zone 67, i.e., from the lower surface 61B toward the upper surface 61A of the web 61. The upper surface 61A of the web 61 corresponds to the upper surface of the web 1 shown by FIG. 1.

Figure 7:
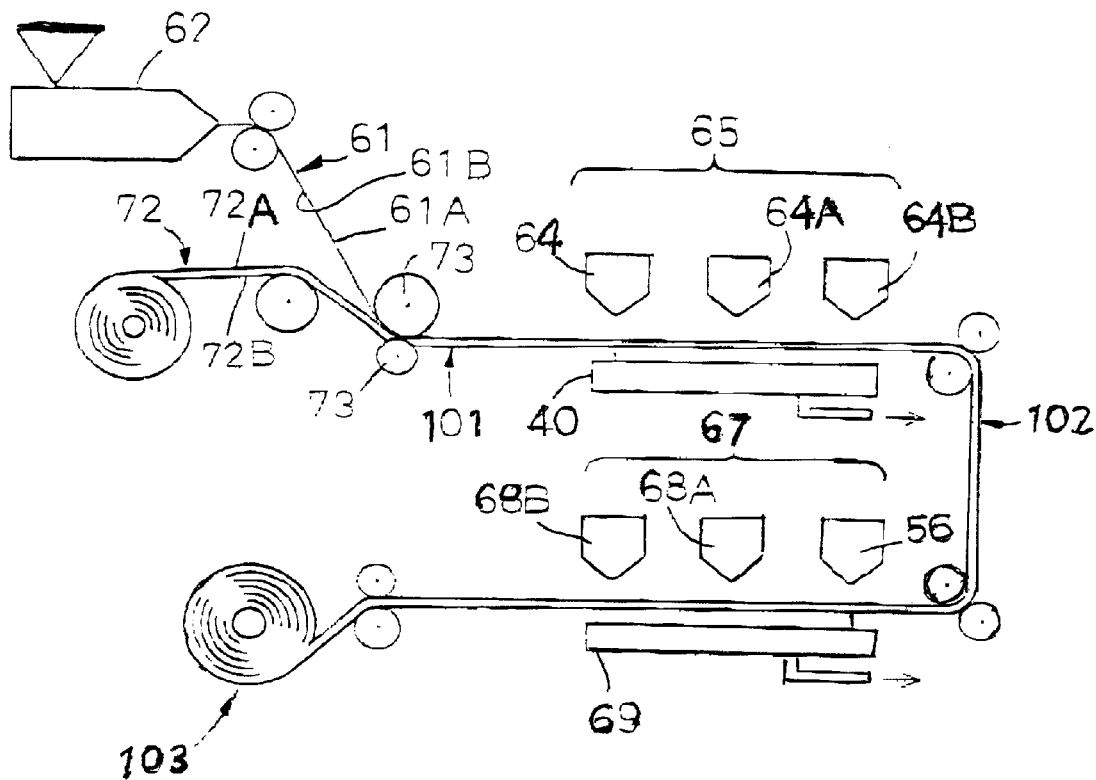
FIG. 7 is a diagram schematically illustrating a manufacturing process for the continuous composite web.
Figure 8:
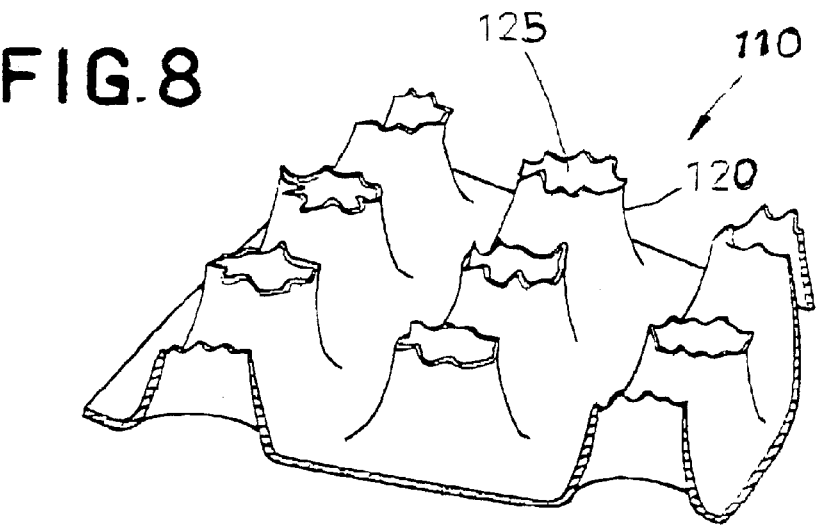
FIG. 8 is a perspective view of a polymeric web manufactured according to the prior art.

FIG. 7 is a diagram exemplarily illustrating a process for manufacturing continuous composite web 100, in which materials as well as the steps similar to those illustrated in FIG. 6 are designated by the similar reference numerals, respectively. A second web 72 comprising sheet-like fibrous assembly destined to form the fibrous layer 2 is continuously fed from the left hand in the diagram. A first web 61 comprising a thermoplastic synthetic resin web discharged from an extruder 62 is placed, in its thermally softened state, upon an upper surface 72A of the second web 72 and fed together into a nip between a pair of pressure rolls 73. In this way, these two webs 61, 72 are bonded together so as to form first composite web 101.

In a first processing zone 65, the first web 61 as one component of the first composite web 101 has its upper surface 61A subjected to a plurality of pillar-shaped water jets supplied from a nozzle array 64 having a plurality of orifices arranged at a predetermined pitch transversely of the first composite web 101. The first web 61 is torn at its spots directly impinged by the pillar-shaped water jets or in the vicinity of these spots and consequently formed with a plurality of intermittent apertures (not shown) longitudinally of the first composite web 101 as the latter travels so as to form a plurality of aperture rows (not shown) extending in parallel one to another transversely of the first composite web 101. In this manner, a continuous second composite web 102 is obtained. The first processing zone 65 may include, in addition to the nozzle array 64, second and third nozzle arrays 64A, 64B adapted to supply pillar-shaped water jets, if necessary to form the aperture rows. These nozzle arrays 64, 64A, 64B are preferably arranged so that corresponding orifices of these nozzle arrays are substantially aligned one with another transversely of the first composite web 101 and therefore the corresponding orifices describe loci which are substantially placed one upon another. Below the first processing zone 65, there is provided a suction mechanism 40 adapted to collect the amount of water jetted from the respective nozzle arrays under an effect of suction.

The second composite web 102 is then transported into a second processing zone 67. Similar to the first processing zone 65, the second processing zone 67 includes nozzle arrays 68, 68A, 68B and a suction mechanism 69. The Second web 72 as one component of the second composite web 102 has its lower surface 72B subjected to pillar-shaped water jets. The respective apertures 60 of the first web 61 already formed by the pillar-shaped water jets in the first processing zone 65 now have their peripheral edges deformed in accordance with the direction in which the pillar-shaped water jets are directed, i.e., from the lower surface 61B toward the upper surface 61A of the first web 61. In this manner, a third composite web 103 is obtained. The water jets supplied from the nozzle arrays 68, 68A, 68B preferably describe loci which are substantially aligned with the loci described by the nozzle arrays 64, 64A, 64B in the first processing zone 65.

The third composite web 103 is taken up on a reel or cut into a desired size so as to obtain the composite web 100 as shown by FIG. 4. The first and second webs 61, 72 in the third composite web 103 correspond to the polymeric web 1 and the fibrous layer 2 in the composite web 100, respectively, and the aperture and the aperture rows of the first web 61 correspond to the apertures 9 and the aperture rows 11 of the polymeric web 1, respectively. The peripheral edges of the apertures formed by locally tearing of the first web 61 under the effect of the pillar-shaped water jets are destined to form the rising portions 12 of the polymeric web 1.

Both in the first and second processing zones 65, 67 illustrated in FIGS. 6 and 7, respectively, it is preferable that the nozzle has a diameter of 50~150 μm, each pair of the adjacent nozzles are spaced from each other at a pitch of 0.2~2 mm, a water pressure is selected within a range of 30~200 kg/cm$^2$ and a suction pressure is selected within a range of 200~1000 mm H$_2$O. Both in the zones 65, 67, the respective webs to be processed are transported in a desired direction on suitable supports such as mesh screens.

Referring to the process illustrated by FIG. 7, if the first and second webs 61, 72 are fed at a room temperature, these webs 61, 72 may be subjected to a pressure heat-sealing between a pair of heated rolls in order to obtain the first composite web 101. Alternatively, these first and second webs 61, 72 may be bonded together by means of suitable adhesive agent such as hot melt adhesive to obtain the first composite web 101.

If it is necessary, the first and second webs 61, 72 may be made hydrophilic at suitable steps of the process illustrated by FIG. 7. The first web 61 may be replaced by a film which is being uniaxially stretched along a machine direction in which the film travels in order to facilitate the intermittent apertures to be obtained.

The invention allows the polymeric web and/or the composite web thereof to be used not only as the liquid-permeable topsheet but also as the liquid-impermeable topsheet in various disposable garments such as diapers, sanitary napkins, training shorts, diapers for incontinent patient and pads of various types.

For adoption of the polymeric web and/or the composite web thereof in the garments as have been described above, principally its orientation is not important. However, particularly when these polymeric web and/or composite web thereof are adopted as the topsheet in the garments, these web are preferably oriented so that the aperture rows as well as the rising portions may extend longitudinally of the garments and body exudates discharged on the garments may flow and spread longitudinally of the garments.

The invention allows the polymeric web to be easily flexed along the aperture rows with a relatively high drapeability, since the polymeric web is provided on its upper surface with a plurality of aperture rows extending in one direction and the peripheral edges of the respective apertures are formed with the undulating fine and deformable rising portions. The invention allows also the surface gloss peculiar to the smooth polymeric web to be effectively suppressed so as to provide a soft velvet touch.

The composite web obtained by joining the fibrous layer to the lower surface of the polymeric web well maintains the comfortable touch provided by the upper surface of the polymeric web and at the same time increase a thickness and a tear strength sufficient to handle the composite web without an excessive carefulness.

By forming the composite web with the liquid guiding passages, the liquid-permeability can be improved without loss of the comfortable touch provided by the upper surface of the web.

What is claimed is:

1. A method for manufacturing an apertured web composed of a flexible apertured polymeric web as a first web having upper and lower surfaces, a flexible fibrous sheet as a second web having upper and lower surfaces, said upper surface of said second web being joined to said lower surface of said first web, and a plurality of portions of said first web which raise from said upper surface thereof so as to make said upper surface of said first web rough, said method comprising the steps of:

a. continuously feeding said first web in a first direction;
   b. continuously feeding said second web in said first direction so that the upper surface of said second web is placed against the lower surface of said first web;
   c. bonding the first and second webs together under a pressure to form a first composite web;
   d. continuously feeding said first composite web in said first direction so that the upper surface of said first web is subjected to pillar-shaped water jets supplied from at least one nozzle having a plurality of orifices arranged transversely of said first direction until said first web is at least locally torn so that said first web is formed with a plurality of apertures in rows extending in parallel one to another in said first direction and a second composite web is obtained; and
   e. continuously feeding said second composite web in said first direction so that, the lower surface of said second web is subjected to pillar-shaped water jets supplied from at least one nozzle having a plurality of orifices arranged transversely of said first direction, until peripheral edges of said apertures are partially deformed upward from said lower surface of said first web.

2. The method according to claim 1, wherein said step b comprises a step of pressing said first web in a thermally softened state against said second web.

3. The method according to claim 1, wherein said step b comprises a step of feeding said first web together with second web into a nip between a pair of heated rolls to heat-seal these two webs together.

4. The method according to claim 1, wherein said step b comprises a step of bonding said first and second webs together by means of adhesive agent.

5. The method according to claim 1, wherein said first web includes fibers selected from the group consisting of thermoplastic synthetic fibers, chemical fibers, natural fibers, and combinations thereof.

6. The method according to claim 1, further including a step of making said second web hydrophilic.

7. The method according to claim 1, wherein the pillar-shaped water jets in steps d and e have loci which are aligned with one another.

8. The method according to claim 1 wherein in step d the first web is repeatedly subjected to said pillar-shaped water jets.

9. The method according to claim 1 wherein in step e said lower surface of said second web is repeatedly subjected to said pillar-shaped water jets.

10. The method according to claim 8 wherein in step e said lower surface of said second web is repeatedly subjected to said pillar-shaped water jets.

* * * * *